United States Patent
Lavelle

(10) Patent No.: US 7,550,012 B2
(45) Date of Patent: Jun. 23, 2009

(54) STENT FOR IMPLANTATION

(75) Inventor: Shay Lavelle, Anacotty (IE)

(73) Assignees: Cook Ireland Limited, Limerick (IE); Vance Products Incorporated, Spencer, IN (US)

( * ) Notice: Subject to any disclaimer, the term of this patent is extended or adjusted under 35 U.S.C. 154(b) by 643 days.

(21) Appl. No.: 11/218,210

(22) Filed: Aug. 31, 2005

(65) Prior Publication Data

US 2007/0078446 A1   Apr. 5, 2007

(51) Int. Cl.
*A61F 2/04* (2006.01)
*A61M 5/00* (2006.01)

(52) U.S. Cl. .................. 623/23.66; 604/8; 623/23.7

(58) Field of Classification Search ....... 623/1.11–1.22, 623/23.66; 606/191, 113; 604/8
See application file for complete search history.

(56) References Cited

U.S. PATENT DOCUMENTS

| | | | |
|---|---|---|---|
| 2,264,988 A | 12/1941 | Lee | |
| 4,713,049 A | 12/1987 | Carter | |
| 4,813,925 A | 3/1989 | Anderson, Jr. et al. | |
| 4,913,683 A | 4/1990 | Gregory | |
| 4,930,496 A | 6/1990 | Bosley, Jr. | |
| 4,931,037 A | 6/1990 | Wetterman | |
| 4,957,479 A | 9/1990 | Roemer | |
| 5,334,185 A | 8/1994 | Gisey et al. | |
| 5,441,516 A | 8/1995 | Wang | |
| 5,554,189 A | 9/1996 | De La Torre | |
| 5,582,619 A | 12/1996 | Ken | |
| 6,033,413 A | 3/2000 | Mikus | |
| 6,264,611 B1* | 7/2001 | Ishikawa et al. | 600/486 |
| 6,332,892 B1* | 12/2001 | Desmond et al. | 623/1.15 |
| 6,589,262 B1 | 7/2003 | Honebrink et al. | |
| 6,652,536 B2* | 11/2003 | Mathews et al. | 606/113 |
| 6,685,744 B2 | 2/2004 | Gellman et al. | |
| 6,733,536 B1* | 5/2004 | Gellman | 623/23.66 |
| 6,736,839 B2 | 5/2004 | Cummings | |
| 6,746,489 B2 | 6/2004 | Dua et al. | |
| 6,770,101 B2 | 8/2004 | Desmond | |
| 6,887,215 B2 | 5/2005 | McWeeney | |

(Continued)

FOREIGN PATENT DOCUMENTS

CA        2264988        9/1999

(Continued)

OTHER PUBLICATIONS

International Search Report from PCT application No. PCT/US2006/033944 dated Jan. 12, 2007 (4 pages).

(Continued)

*Primary Examiner*—Suzette J Gherbi
(74) *Attorney, Agent, or Firm*—Brinks Hofer Gilson & Lione

(57) ABSTRACT

A stent is made from a coiled wire and is very smooth along its length and as well its ends. The stent is thus highly atraumatic to patients, and because of its smooth surfaces, it presents a surface to which it is difficult for microbes to cling. The stent may be used in a minimally invasive procedure, such as for a ureteral stent, and may also be used percutaneously. Similar stents may be used in other body areas, such as in draining the biliary tract, the gastro-intestinal tract, hepatic procedures, and in vascular procedures as well.

19 Claims, 5 Drawing Sheets

U.S. PATENT DOCUMENTS

| | | | |
|---|---|---|---|
| 7,044,981 B2 * | 5/2006 | Liu et al. | 623/23.66 |
| 2001/0018574 A1 | 8/2001 | Toledo et al. | |
| 2002/0183852 A1 | 12/2002 | McWeeney | |
| 2004/0078088 A1 | 4/2004 | Gellman | |
| 2004/0087886 A1 * | 5/2004 | Gellman | 604/8 |
| 2004/0127918 A1 | 7/2004 | Nikolchev et al. | |
| 2004/0181186 A1 | 9/2004 | Gellman et al. | |
| 2005/0234388 A1 * | 10/2005 | Amos et al. | 604/8 |
| 2005/0240278 A1 * | 10/2005 | Aliski et al. | 623/23.7 |
| 2007/0021840 A1 | 1/2007 | Lopera | |
| 2007/0078511 A1 | 4/2007 | Ehr et al. | |
| 2007/0276466 A1 * | 11/2007 | Lavelle et al. | 623/1.22 |
| 2008/0086215 A1 * | 4/2008 | St. Pierre | 623/23.66 |
| 2008/0133025 A1 | 6/2008 | Daignault et al. | 623/23.7 |
| 2008/0183299 A1 * | 7/2008 | Monga et al. | 623/23.66 |
| 2008/0208083 A1 * | 8/2008 | Lin et al. | 601/2 |

FOREIGN PATENT DOCUMENTS

| | | |
|---|---|---|
| EP | 0 365 269 A1 | 4/1990 |
| EP | 0 365 269 B1 | 3/1994 |
| WO | WO 03/079930 A1 | 10/2003 |

OTHER PUBLICATIONS

International Preliminary Examination Report dated Mar. 13, 2008 for related PCT application PCT/US2006/33944.

Canadian Intellectual Property Office Examiner's Report dated Aug. 20, 2007 (4 pages).

Office Action dated Dec. 26, 2008 for U.S. Appl. No. 11/513,445.

Office Action dated Jan. 22, 2009 for related U.S. Appl. No. 11/748,323.

* cited by examiner

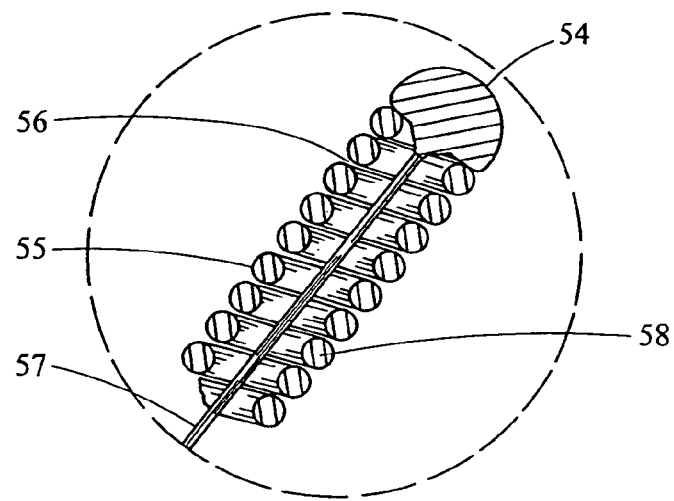
Fig. 5A
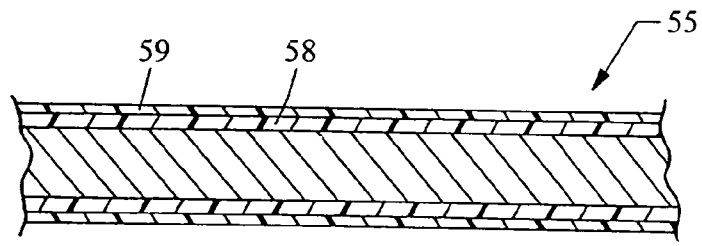
Fig. 5B
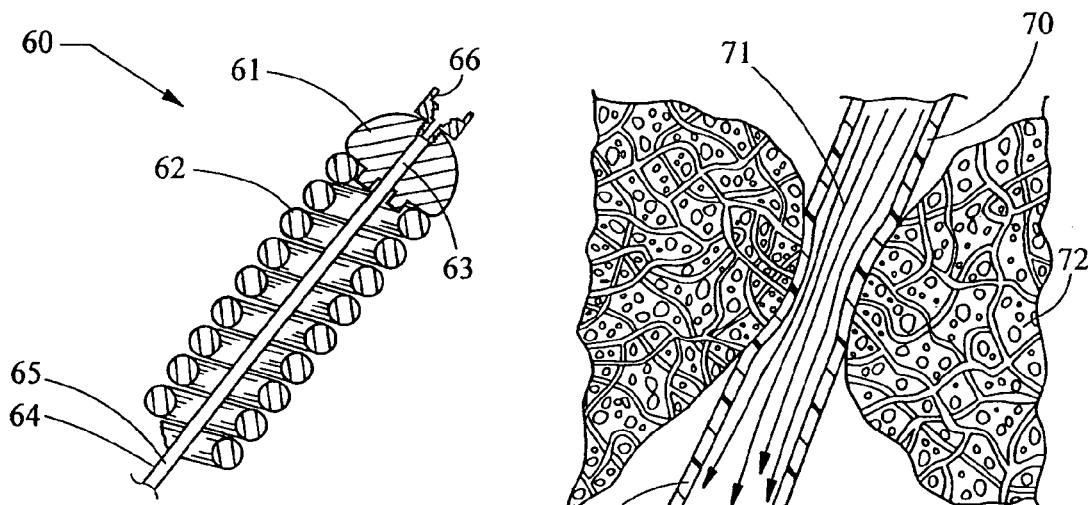
Fig. 5C
Fig. 6

STENT FOR IMPLANTATION

RELATED APPLICATION

This application is related to U.S. Provisional Appl. 60/713,151, entitled, Coaxial Dilatation Method for Stent Implantation, filed the same day as the present application.

TECHNICAL FIELD

The technical field of the invention is implantable medical devices, and in particular a stent useful for urinary drainage.

BACKGROUND

Minimally-invasive surgery has evolved to a point where procedures that were unimaginable a few years ago are now routinely performed on a daily basis. Even in these procedures, however, there is room for improvement. One example is the removal of stones and calculi from kidneys and ureters, to the great relief of many suffering patients.

To treat this condition, several individual steps are involved. In one procedure, these steps include placing a relatively narrow guidewire through a urethra and a bladder, and then through the ureter and into the kidney. After the guidewire is placed, a catheter is run along the guidewire, dilating the body passages (the urethra and the ureter) as it moves down the guidewire. In the next sequence for this procedure, a ureteral access sheath is guided along and down the guidewire and the catheter. The access sheath also dilates the body passages as it moves from outside the body, through the urethra, and into the ureter, down to the desired location, and into or very near the kidney.

The physician may then remove calculi and stones through the access sheath, using a grasper, a retrieval basket or other device. The access sheath protects the ureter from repeated passage of the retrieval device while the stones or calculi are removed. After the stones are removed, a ureteral stent may be placed into the ureter through the access sheath, using the catheter or a pushing tube to position the stent. The stent is used to retain patency of the ureteral lumen and to continue normal urinary drainage.

One problem with this procedure is that the guidewire may need to be very long in order for the physician to control passage first of the catheter and then of the access sheath to the desired location within the patient's body. Very long guidewires are not standard, and it may require two people to handle such a guide wire so that it does not drape onto the floor. The surgeon may decide he or she needs a guidewire with a stiffness different from the one provided with the particular kit in order to negotiate the pathway. A substitute stiffer guidewire may not be readily available in non-standard lengths.

Using this procedure for sequential placement of first a catheter and then an access sheath, the guidewire needs to be as long as the combination of both the catheter and the access sheath. A long guidewire leads to two problems, including a greater tendency to kink, and a need for greater skill on the part of the physician to maneuver the guidewire while placing the guidewire itself, the catheter, and the sheath.

Another problem that is encountered with ureteral stents occurs in cancer patients, where a growth may apply radial compression to a ureter. Such compression can make fluid flow difficult. In these cases, a typical polymeric, relatively soft pig-tail stent may not have sufficient radial strength to resist compression by a cancerous or other growth. In these cases, a stronger, sturdier ureteral stent is needed to resist radial compression and allow for continued drainage from the kidney to the bladder. In some cases, a urethral stent or catheter may also be helpful to ensure drainage from the bladder. What is needed is a better way to dilate the body passages in order to place the access sheaths and stents.

BRIEF SUMMARY

This need is met by embodiments of the present invention. One embodiment of the present invention is a kit for placing a stent. The kit includes a wire guide, a catheter securable to an access sheath, the catheter further comprising a connector at a proximal end of the catheter, and a stent for placing in a body passage of a patient through the access sheath. The stent comprises a hollow coiled wire with an internal lumen, the internal lumen communicating outside the coiled wire through small spaces between adjacent coils, and wherein the stent further comprises a distal end with a distal pigtail portion and a proximal end with a proximal pigtail portion, each pigtail portion comprising an end-cap, the end caps secured to the wire and joined to an internal rod.

Another embodiment is a stent. The stent includes a hollow coiled wire having an internal lumen, the internal lumen communicating outside the coiled wire through small spaces between adjacent coils, the coiled wire further comprising a distal pigtail portion and a proximal pigtail portion. The stent also includes a distal cap on a distal end and a proximal cap on a proximal end of the coiled wire, the caps secured to the wire and also secured with a rod between the caps.

Another embodiment is a method of preparing a stent suitable for implantation. The method includes steps of winding a wire coil, inserting a rod into the wound coil, attaching at least one end cap to the coil or to the rod, and electropolishing the stent. There are many embodiments of the kit and stents according to the present invention, of which only a few are described herein. The accompanying drawings and descriptions are meant to be illustrative rather than limiting.

BRIEF DESCRIPTION OF THE DRAWINGS

FIGS. 5, 5a and 5b depict a ureteral stent useful in kit embodiments;

FIG. 5c depicts a second embodiment of a stent; and

FIG. 6 depicts a stricture in a body lumen.

DETAILED DESCRIPTION OF THE DRAWINGS AND THE PRESENTLY PREFERRED EMBODIMENTS

Figure 1:
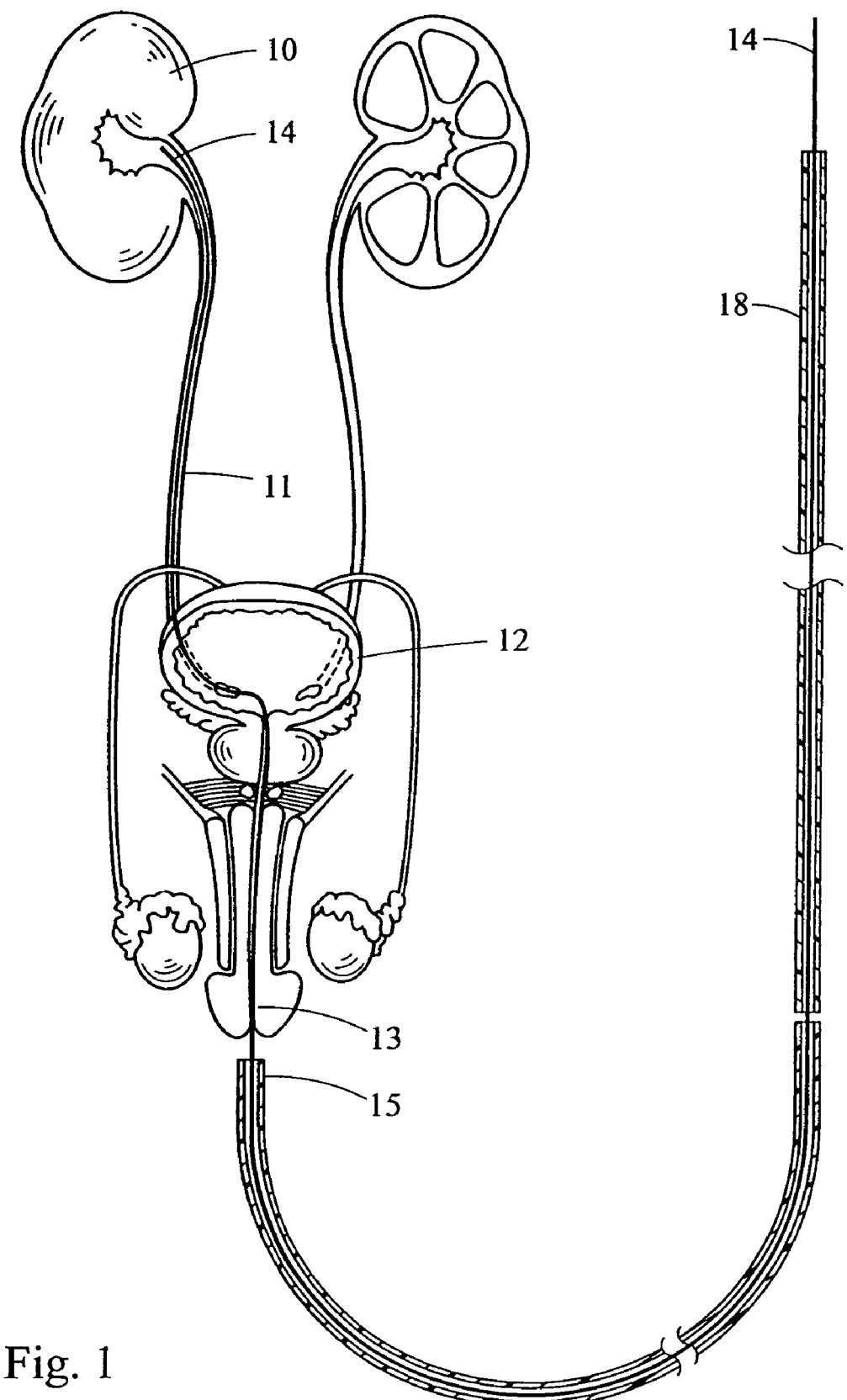
FIG. 1 is an illustration of a present technique for ureteral stent placement.
Figure 2:
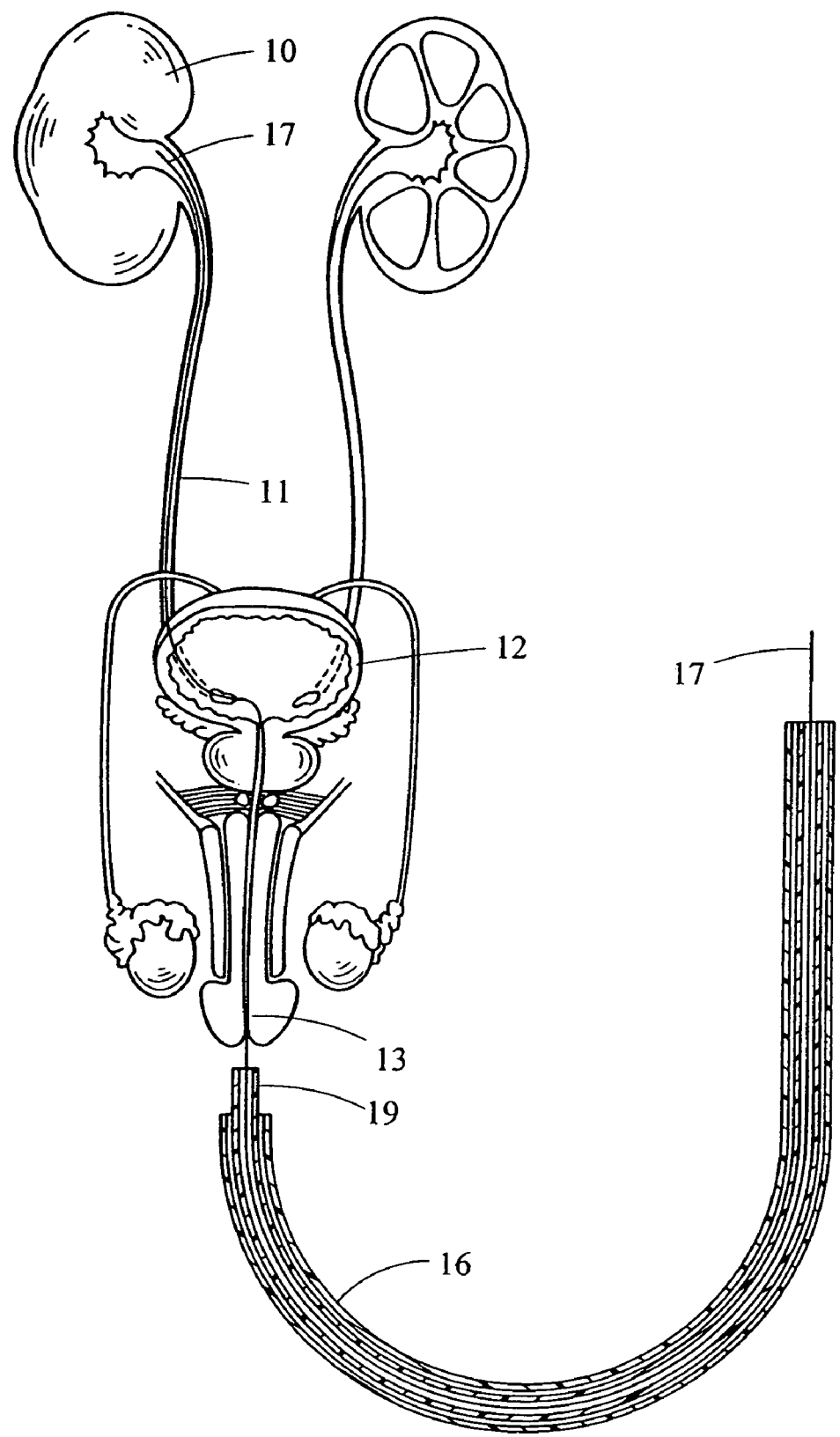
FIG. 2 is an illustration of a technique for dual dilatation.

FIGS. 1 and 2 illustrate the differences in technique between a present method for ureteral stent placement and a new method of coaxial dual dilatation. In both figures, a physician desires to perform a procedure upon a kidney 10. In FIG. 1, a guidewire 14 is advanced through a urethra 13, a bladder 12, and a ureter 11 to the kidney on which the procedure is to be performed. In order to accomplish this, the wire guide is placed, and a ureteral stent 15 is guided along the guidewire, extending as far as desired, typically into the kidney by means of a pushing tube 18 that is also placed along the guidewire as shown. The physician places the stent by passing first the guidewire, and then passing the ureteral stent and the pushing tube over the guidewire. The urethra may be dilated separately to accommodate an instrument such as a cystoscope to aid the surgeon.

The guidewire is typically between 0.018 to 0.038 inches in diameter (about 0.46 mm to 0.97 mm). The catheter may be 4-8 Fr. The ureteral stent may be used for patency of the ureteral lumen. In order to achieve this dilatation, however, a very long wire guide was needed to extend the length of the both the catheter and the access sheath, where the access sheath is capable of extending to the ureteropelvic junction. This may lead to kinking and may also lead to difficulty in the physician controlling the wire guide as he or she must control the entire length of the wire guide while sequentially running the catheter and the access sheath down the wire guide.

An improved method is illustrated in FIG. 2. In this method, a physician places a wire guide 17 through a urethra 13, a bladder 12, and a ureter 11 into a kidney 10. After the wire guide is placed, a catheter 19 secured to an access sheath 16 is guided along the wire guide, the catheter and access sheath combination coaxially "dual dilating" at least the proximal portion of the ureter. This coaxial dilatation procedure enables the physician to use a shorter wire guide, e.g., using a 145 or 150 cm wire guide rather than a wire guide that may have to be 220 cm or even longer, perhaps 250-260 cm. This may also shorten the time required to position the access sheath, and thus shorten the actual time spent in the therapeutic procedure and reduce the number of personnel required. The access sheath and the catheter are advanced to the desired location, e.g., into the calices of a kidney. The catheter may then be removed and replaced by a stent. The stent is then implanted by a surgeon pushing on a stent positioner, such as a catheter or other pushing device of appropriate diameter and length. The sheath is then retracted while the positioner or other device is used to keep the stent in place.

In addition to the method shown in FIG. 2, there are other ways to practice the invention. For instance, rather than accessing the ureter through the urethra and bladder, a physician may use a nephrostomy method, in which the access sheath and catheter are advanced through a person's skin to reach the calices of the kidney directly. If a path to a bile duct is needed, the physician may access the bile duct through an endoscope via the mouth, esophagus, stomach and intestines, or via laparoscopic methods directly through the skin (percutaneous). If vascular access is desired, a physician may access the blood vessel through an opening, such as an opening manufactured in the femoral artery.

Figure 3:
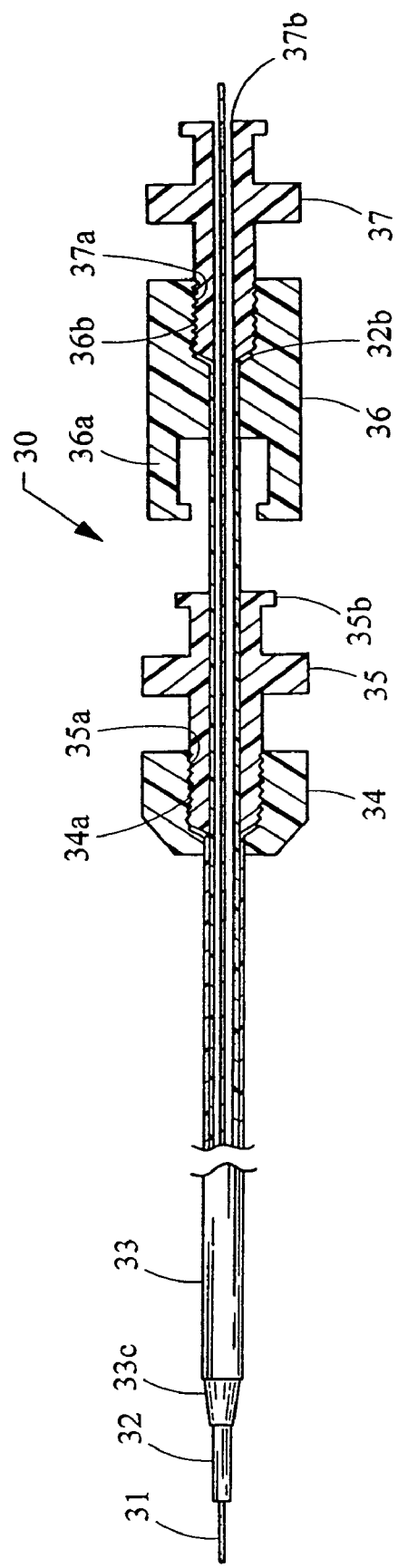
FIG. 3 is a cross-sectional view of a first embodiment of a kit according to the present invention.
Figure 3A:
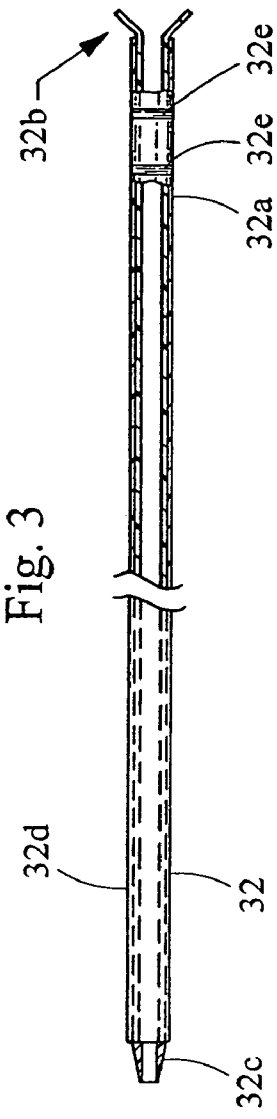
FIGS. 3a and 3b depict a catheter and a sheath useful in kit embodiments.
Figure 3B:
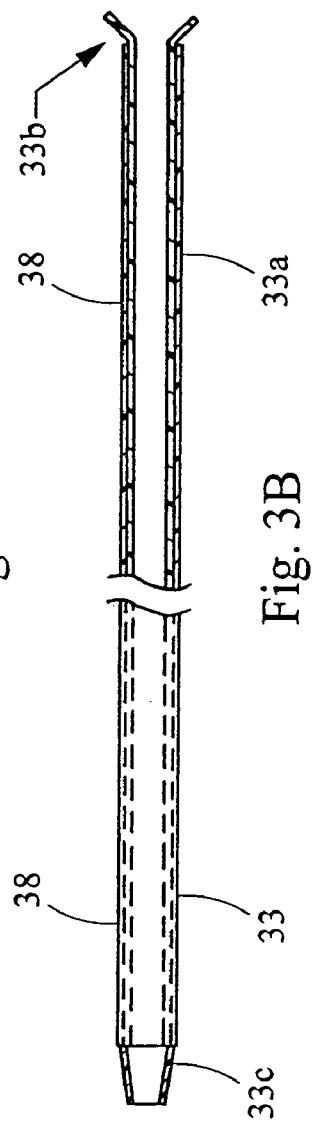

An embodiment of a kit useful in the above procedure is depicted in FIGS. 3, 3a and 3b. The kit includes a wire guide 31, which may be shorter than a wire guide used for a sequential procedure as described above. A wire guide with a length of about 145-150 cm is preferred, but other lengths may be used. A catheter 32 is included, the catheter preferably having a proximal end 32a with a flared tip 32b, and a soft rounded/tapered non-traumatic tip 32c for protection of the patient. Materials for the catheter are typically plastic or elastomeric materials, e.g., PVC, PTFE, polyurethane, silicone, and urethane, but any medically acceptable materials may be used. Catheters suitable for this use are preferably about 50-85 cm long. The tip is flared for ease in securing to connectors and in sealing with connectors so that the catheter may deliver a fluid, such as a radiopaque fluid for diagnostic procedures or for visualization purposes. The catheter may have a hydrophilic coating 32d on at least part of its outer surface. The proximal portion may also have one or more marking bands 32e to assist the physician in deploying the stent.

Catheter 32 may interface with one or more connectors 36 for mating with syringe adapter 37 (such as a female Luer lock adapter) so that a syringe (not shown) can inject the radiopaque fluid. Connector 36 may include a male Luer lock fitting 36a on a distal end of connector 36 and internal threads 36b on its proximal end. Male Luer lock connection 36a may be used to connect first connector 36 to second connector 35. Threads 36b may interface with matching external threads 37a of syringe adapter 37 for delivery of a fluid through lumen 37b. Flared end 32b of the catheter helps to seal the connection between connector 36, catheter 32, and syringe 37. While the Luer lock and threaded connections depicted and described are preferred, other connectors may be used instead. For example, quick-release connectors could be used to secure the catheter or sheath to their proximal fittings. When connectors 36 and 37 are joined with flared end 32b, a leak-tight connection is formed, and the catheter may reliably deliver fluid without undesirable leakage.

Access sheath 33 includes a proximal portion 33a and an end portion with a flared tip 33b. The access sheath also includes a distal end 33c, preferably atraumatic, soft and rounded or tapered for ease of introduction into the patient. Distal end 33c of the access sheath is also preferably more highly radiopaque than the remainder of the access sheath, so that the end may be observed with x-ray or fluoroscopic detection means during the implantation procedure. Flared tip 33b helps to seal an interface between access sheath 32 and connector 34. Access sheaths are preferably are made from low friction polymers (e.g. PTFE, FEP etc.) with reasonable radial compressive strength—wire reinforcement can be added to the sheath for extra radial strength. Suitable access sheaths sold under the name of Check-Flo® II Introducer sheaths sold by Cook Incorporated, Ind. may be used. Also Flexor® sheaths available from Cook Urological Incorporated of Spencer, Ind. may be used. In this application the sheath is typically 70 cm long so to extend from the urethral meatus to the ureteropelvic junction. The access sheath is generally just slightly larger in inner diameter than the outer diameter of the catheter, e.g. 0.5 Fr. If catheter 32, as shown in FIG. 3 and preferably with a blunt distal tip, is the same size diameter as the stent, the catheter may be used as a stent positioner, with the physician simply butting the distal end of the catheter against the proximal end of the stent so that the positioner can be used to push the stent into position.

Connector 34 may include internal threads 34a for connecting to Luer lock connector 35 having female Luer lock connection 35b. While Luer lock connections and connectors are preferred, other connectors and other types of medically-acceptable connectors may be used. At least a distal portion of sheath 33 may also include a hydrophilic coating 38.

The fittings described above may be used to connect access sheath 32 with catheter 33. To help insure that access sheath 32 seals securely, connector 34 may be temporarily joined to connector 35 with an adhesive. Other methods may also be used, such as securely tightening connectors 34, 35 together. Joining the female Luer lock connection 35b to male Luer lock connection 36a reliably secures access sheath 32 to catheter 33 for insertion or for removal. By breaking the connection between connectors 35, 36 after insertion, catheter 32 may be removed and the access sheath may be used for other purposes. These other purposes may include diagnostic purposes, such as insertion of an endoscope, or therapeutic procedures, such as breaking up stones or calculi, using a holmium laser or other type of lithotripter. A grasper or basket may then be inserted into the working channel of the endoscope to remove the fragments. In the same manner, connectors 36, 37 may also be temporarily joined with an adhesive to prevent easily breaking the connection. By adhering connector pairs 34, 35 and 36, 37, it is easier for the surgeon to make and break the Luer lock connection between connectors 35, 36.

In the assembled view of FIG. 3, note that the catheter may be longer than the access sheath, and may extend slightly further distally than the access sheath. Nevertheless, the sheath and the catheter are substantially coaxial, i.e., catheter 32 runs the entire length of access sheath 33. Substantially coaxial means that substantially the length of one of the sheath and the catheter is coaxial with the other of the sheath and the catheter during the procedure for implanting a stent or other device into a human or mammalian body.

Figure 4:
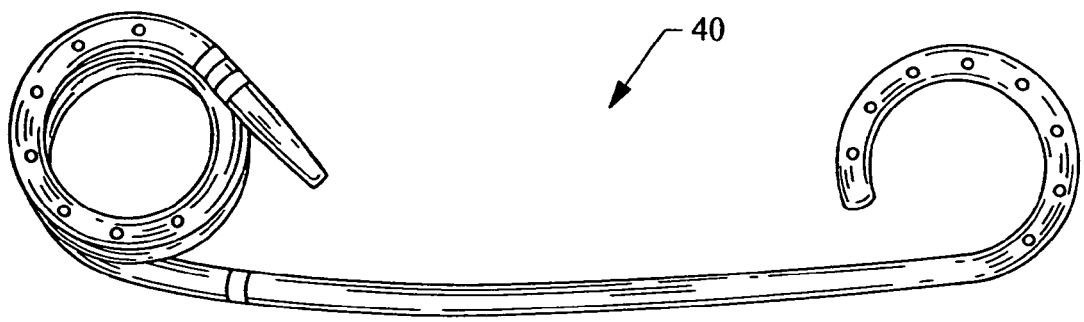
FIG. 4 depicts a pigtail ureteral stent.

The access sheath may also be used to place a ureteral stent when the above diagnostic or therapeutic procedures are completed. No matter how gentle the procedures described above, there is a chance of some amount of trauma to the ureter during the procedures. Accordingly, it may be prudent to place a stent into the ureter to maintain patency of the ureteral lumen. Ureteral stents may be of the "double pigtail" variety, such as those available from Cook Urological Incorporated, Spencer, Ind. FIG. 4 depicts one such stent 40. These ureteral stents are typically available in sizes of 4 Fr to 8 Fr and may be placed into a ureter using a wire guide and the procedure described above.

The procedure described above for dual, coaxial dilatation may be especially useful when there is a stricture or narrowing of a ureter for any reason. FIG. 6 depicts one such case. In FIG. 6, ureter 70 is constrained from its normal width 73 into a narrower path 71 along part of its length by a constricting body mass 72. An example would be a cancerous growth near the ureter that would cause compression on the ureter, e.g., colon cancer, bladder cancer, ovarian cancer, endometrial cancer, cervical cancer, and the like. In such cases, a stent with greater radial strength may be needed in order to maintain its lumen and allow drainage of urine through the ureter. Instead of elastomeric or plastic stents, a stent made from material that is more resistant to deformation may be needed. In addition, the stent must be removable without significant deformation or resistance.

Figure 5:
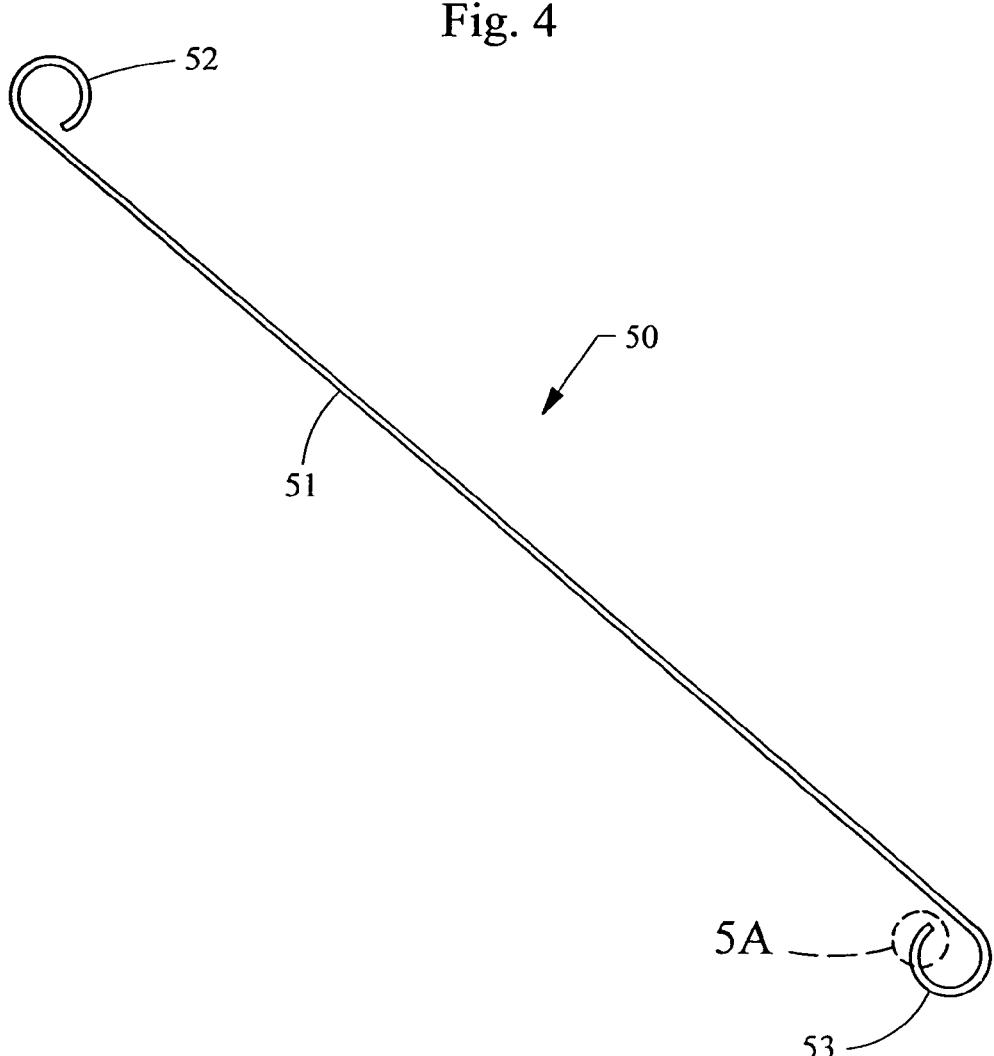

Such a stent is depicted in FIGS. 5, 5*a*, and 5*b*. Stent 50 is made from coiled wire along its length 51 and at both distal and proximal ends 52, 53, which may be substantially the same or may be different. The coils should be closely spaced so that they touch, but still allow fluid, such as urine or bile, to flow through the coils. The coils should also be spaced closely enough so that no tissue ingrowth occurs. Materials used in these stents are preferably biocompatible and corrosion-resistant. The wire is preferably made from alloys with minimal or low magnetic properties to avoid interference with diagnostic equipment, such as MRI machines. Alloys such as MP35N, MP 159, Astroloy M, Inconel 625, 316 stainless steel, 35N LT, Biodur 108, pure titanium, and Hastelloy S are preferred.

An inner wire 57 extends throughout the length of the stent and is secured to both ends 52, 53, such as by welding, brazing or swaging to a tip 54 on each end. The tips and the wire are preferably made from the same metallic alloy as the coil. The tips may be formed into a molten domed mass from the coiled wire and the inner wire during the joining process. It is important that both ends be atraumatic to the patient. The coils 55 have small gaps 56 between them so that urine may soak or leak into the stent in the kidney area or anywhere along the ureter and may leak out of the coils in the ureter or bladder area. The internal wire is helpful in preventing unraveling or extension of the coils, especially when the stent is being removed. The portion of the stent between the pigtails is preferably about 20 cm to about 32 cm long. Other lengths may be used.

In order to present a surface highly resistant to encrustation during long-term implantation, stent embodiments should be highly polished, preferably electro-polished. In electro-polishing, the article to be polished is placed into an electrolytic bath, but instead of being plated, the current is reversed. Asperities, tiny projections of metal on the surface of the stent coils, are vulnerable to this process, and are removed without changing the dimensions or temper of the stent. This highly polished surface is believed to be resistant to the bacteria responsible for encrustation because there are fewer sites of surface roughness suitable for adherence.

The wire 55 used for the outer coils is preferably coated, such as with a fluoropolymer or other protective, lubricious coating 58 before it is wound into a coil. It is preferred that the entire coil length be coated, while preserving the small gaps between the coil-turns of the stent for functioning of the stent drainage mechanism. In addition, a layer 59 of a preventive or other medication may be applied over coating 58, such as a layer containing heparin or other drug. Heparin tends to resist encrustation with long-term implantation of urinary tract medical devices. Heparin or other drug-containing coatings are preferably applied after the coil is wound. Fluoropolymers such as PTFE help to enable the bonding of certain drugs, such as heparin, to the surface of the coils and are therefore desirable in stents intended for long-term implantation. Other drugs useful for discouraging encrustation include heparin, covalent heparin, dexamethazone, dexamethasone sodium phosphate, dexamethasone acetate and other dexamethasone derivatives, triclosan, silver nitrate, ofloxacin, ciproflaxin, phosphorylcholine and triemethoprim.

In one preferred embodiment, the wire for coiling is coated, as by extrusion, with a fluoropolymer or other lubricious polymer or plastic material, and is then wound into a coiled stent, complete with end caps and a coated internal wire. The stent is then immersed into a solution of heparin, and a partial vacuum is applied to the vessel containing the solution. Preferred is a vacuum of 10 Torr or less for a time period of about one minute to one hour, depending on the amount of coating desired. The stents are then rinsed in distilled water and dried before being packaged.

Another embodiment of a stent with greater radial strength is depicted in FIG. 5*c*. In this embodiment, which is similar to the embodiment of FIG. 5*a*, a narrow hollow cannula 64 extends between the distal and proximal ends of the stent 60. Stent 60 includes metallic ends 61 which include an orifice 63 to accommodate cannula 64. The stent includes a hollow outer coil 62 for greater radial strength. Cannula lumen 65 may be used to enable placement by a wire guide, and also may act as a lumen for drainage of body fluids, such as urine or bile. Fluid connector 66 may be attached to a proximal end of the cannula for connection for fluid drainage or for infusion of diagnostic or therapeutic fluids. The fluid connector may be attached by threads, by soldering or brazing, by or by any convenient method.

In addition, one or more additional medications or drugs may be placed on the surface of the stent in order to assist in patient care and comfort. For instance, an antimicrobial drug, such as a combination of rifampin and minocycline, may help to reduce inflammation and microbial activity in the vicinity of the stent. Antimicrobial coatings applied to the stent may include the following drugs, or their salts or derivatives: rifampin, minocycline, a mixture of rifampin and minocycline, a non-steroidal anti-inflammatory agent, a penicillin, a cephalosporin, a carbepenem, a beta-lactam, an antibiotic, an aminoglycoside, a macrolide, a lincosamide, a glycopeptide, a tetracyline, a chloramphenicol, a quinolone, a fucidin, a sulfonamide, a trimethoprim, a rifamycin, an oxaline, a streptogramin, a lipopeptide, a ketolide, a polyene, an azole, an echinocandin, alpha-terpineol, methylisothiazolone, cetylpyridinium chloride, chloroxyleneol, hexachlorophene, chlorhexidine and other cationic biguanides, methylene chloride, iodine and iodophores, triclosan, taurinamides, nitrofurantoin, methenamine, aldehydes, azylic acid, rifampycin, silver, benzyl peroxide, alcohols, and carboxylic acids and salts, and silver sulfadiazine. Also useful as antimicrobials are anthracyclines, such as doxorubicin or mitoxantrone, fluoropyrimidines such as 5-fluoroacil, and also podophylotoxins, such as etoposide. The salts and the derivatives of all of these are meant to be included as examples of antimicrobial drugs.

Analgesics, such as aspirin or other non-steroidal anti-inflammatory drugs, may also be applied to the surface to reduce pain and swelling upon implantation of the stent. These drugs or their salts or derivatives may include aspirin and non-steroidal anti-inflammatory drugs, including naproxen, choline, diflunisal, salsalate, fenoprofen, flurbiprofen, ketoprofen, ibuprofen, oxaprozin, diclofenac, indomethacin, sulindac, acetoaminophen, tolmetin, meloxicam, piroxicam, meclofenamate, mefanimic acid, nabumetone, etodelac, keterolac, celecoxib, valdecoxib and rofecoxib, mixtures thereof, and derivatives thereof.

Other analgesics or anesthetics that may be coated onto the surface of the stent include opioids, synthetic drugs with narcotic properties, and local anesthetics to include at least paracetamol, bupivacaine, ropivacaine, lidocaine, and novacaine.alfentanil, buprenorphine, carfentanil, codeine, codeinone, dextropropoxyphene, dihydrocodeine, endorphin, fentanyl, hydrocodone, hydromorphone, methadone, morphine, morphinone, oxycodone, oxymorphone, pethidine, remifantanil, sulfentanil, thebaine, and tramadol, mixtures thereof, and derivatives thereof.

Any of these drugs and coatings are preferably applied in a time-release manner so that the beneficial effect of the drug is sustained over a period of at least several weeks or months. This may be especially helpful in the case where a stent or catheter will remain in place for a considerable length of time.

While the present stent is highly useful for drainage of the kidneys, similar stents may be used in other hollow parts of the body. These may include procedures, hepatic drainage, gastro-intestinal drainage, and so on, for drainage of other body cavities. It is intended that the foregoing detailed description be regarded as illustrative rather than limiting, and that it be understood that it is the following claims, including all equivalents, that are intended to define the spirit and scope of this invention.

What is claimed is:

1. A kit for placing a stent, the kit comprising:
   a wire guide;
   a catheter securable to an access sheath, the catheter further comprising a connector at a proximal end of the catheter; and
   a stent configured for placing in a body passage of a patient, wherein the stent comprises a hollow coiled wire with an internal lumen, the internal lumen communicating outside the coiled wire through small spaces between adjacent coils, and wherein the stent further comprises a distal end with a distal pigtail portion and a proximal end with a proximal pigtail portion, each pigtail portion comprising an end-cap, the end caps secured to the wire and joined to an internal rod.

2. The kit of claim 1, wherein the body passage is a ureter, the access sheath is a ureteral access sheath, the catheter is suitable for advancing through the ureter, and the stent is a ureteral stent.

3. The stent of claim 1, wherein the internal rod is hollow and comprises a lumen extending through the rod and the end caps.

4. The stent of claim 1, wherein the stent has been smoothed by an electropolishing process, and further comprising a coating applied to the wire or to the stent.

5. The kit of claim 1, further comprising a coating on the stent, the coating comprising an antimicrobial, antiencrustation, analgesic or anesthetic compound.

6. The kit of claim 1, further comprising a coating applied via a vacuum process.

7. A stent, comprising:
   a hollow coiled wire, the coil having an internal lumen, the internal lumen communicating outside the coiled wire through small spaces between adjacent coils, the coiled wire further comprising a distal pigtail portion and a proximal pigtail portion; and
   a distal cap on a distal end and a proximal cap on a proximal end of the coiled wire, the caps secured to the wire and also secured with a rod between the caps.

8. The stent of claim 7, wherein at least one of the hollow coiled wire and the internal wire are made from MP35N or MP 159.

9. The stent of claim 7, further comprising a first coating on the wire or on the stent, and a second coating of a drug.

10. The stent of claim 7, wherein the rod is hollow and further comprises a lumen extending through the rod and communicating with at least one orifice in one of the caps.

11. The stent of claim 7, wherein the rod is hollow and further comprises a lumen extending through the rod and communicating with at least one orifice in at least one of the caps, and a fluid connector connected to the at least one of the caps, the fluid connector communicating with the at least one orifice.

12. The kit of claim 7, further comprising at least one coating on the stent including an antimicrobial, antiencrustation, analgesic or anesthetic compound.

13. A method of preparing a stent suitable for implantation, the method comprising:
   winding a wire coil;
   inserting a rod into the wound coil;
   attaching at least one end cap to the coil or to the rod, wherein the at least one end cap further comprises end caps on a distal end and a proximal end of the stent, each end cap further comprising an orifice, and the rod further comprises a lumen extending through the stent and connected to the end caps; and
   electropolishing the stent.

14. The method of claim 13, further comprising coating the stent with a polymeric or lubricious coating.

15. The method of claim 13, further comprising coating the stent or a polymeric coating of the stent with an anti-encrustation, antimicrobial, analgesic or anesthetic drug.

16. The method of claim 13, wherein the wire is selected from the group consisting of MP35N, MP 159, Astroloy M, Inconel 625, 316 stainless steel, 35N LT, Biodur 108, titanium, and Hastelloy S.

17. The method of claim 13, further comprising a fluid connector attached to at least one of the end caps on the distal end and the proximal end.

18. The method of claim 13, further comprising coating the wire with a coating material.

19. The method of claim 13, further comprising coating the wire or the stent with a coating and then vacuum-impregnating the stent with a coating of heparin or other drug.

* * * * *